(12) United States Patent
Nazareth et al.

(10) Patent No.: US 7,045,342 B2
(45) Date of Patent: *May 16, 2006

(54) DIAGNOSTIC DETECTION DEVICE AND METHOD

(75) Inventors: Albert Nazareth, Mercerville, NJ (US); Mary Beth Boyle, Pennington, NJ (US); Yea-Shun Cheng, Doylestown, PA (US)

(73) Assignee: Church & Dwight Co., Inc., Princeton, NJ (US)

( * ) Notice: Subject to any disclaimer, the term of this patent is extended or adjusted under 35 U.S.C. 154(b) by 16 days.

This patent is subject to a terminal disclaimer.

(21) Appl. No.: 10/794,516

(22) Filed: Mar. 5, 2004

(65) Prior Publication Data

US 2004/0171174 A1    Sep. 2, 2004

Related U.S. Application Data

(60) Continuation of application No. 09/951,007, filed on Sep. 12, 2001, now Pat. No. 6,767,714, which is a division of application No. 08/432,894, filed on May 2, 1995, now Pat. No. 6,319,676.

(51) Int. Cl.
*C12M 3/00*     (2006.01)

(52) U.S. Cl. .................. 435/287.1; 422/56; 422/57; 422/58; 422/61; 435/7.1; 435/7.2; 435/7.5; 435/7.93; 435/7.94; 435/7.95; 435/287.7; 435/287.9; 435/805; 435/810; 435/970; 436/169; 436/514; 436/518; 436/524; 436/530; 436/535; 436/541; 436/810

(58) Field of Classification Search .................. 422/56, 422/57, 58, 61; 435/7.1, 7.2, 7.5, 7.93, 7.94, 435/287.2, 287.7, 287.9, 805, 810, 970, 7.95; 436/169, 518, 514, 524, 530, 535, 541, 810
See application file for complete search history.

(56) References Cited

U.S. PATENT DOCUMENTS

| 3,620,677 | A | 11/1971 | Morison ...................... 23/253 |
| 3,811,840 | A | 5/1974 | Bauer et al. ............. 23/253 TP |
| 3,888,629 | A | 6/1975 | Bagshawe ................. 23/230 B |
| 4,042,335 | A | 8/1977 | Clement ...................... 23/253 |
| 4,045,384 | A | 8/1977 | Dorman ......................... 260/8 |
| 4,048,298 | A | 9/1977 | NiSwender ................ 424/1.5 |
| 4,168,146 | A | 9/1979 | Grubb et al. ................. 23/230 |

(Continued)

FOREIGN PATENT DOCUMENTS

AU    A 63 502/86    10/1886

(Continued)

OTHER PUBLICATIONS

S.C. Lou et al., "One-Step Competitive Immunochromatographic Assay for Semiquantitative Determination of Lipoprotein (a) in Plasma" *Clin. Chem.* 39(4):619-624 (1993).

(Continued)

*Primary Examiner*—Christopher L. Chin
(74) *Attorney, Agent, or Firm*—Stephen B. Shear

(57) ABSTRACT

The invention provides an improved test cell for detecting the presence of an analyte in a liquid sample. The device has an elongate casing defining a liquid sample inlet, a reservoir volume, a test volume, and a window through the casing at the test volume. Disposed within the cell is a sample absorbent, a novel biphasic substrate and a reservoir, together capable of transporting an aqueous solution within the casing along a flow path extending from the sample inlet through the test volume and into the reservoir volume. The invention further comprises a method for detecting the presence of an analyte in a liquid sample using the device and a biphasic chromatographic material for carrying out the method.

19 Claims, 4 Drawing Sheets

U.S. PATENT DOCUMENTS

| | | | | |
|---|---|---|---|---|
| 4,169,138 A | 9/1979 | Jonsson | | 424/12 |
| RE30,267 E | 5/1980 | Bruschi | | 23/230 |
| 4,205,952 A | 6/1980 | Cais | | 23/230 B |
| 4,219,335 A | 8/1980 | Ebersole | | 23/230 B |
| 4,235,601 A | 11/1980 | Deutsch et al. | | 23/230 R |
| 4,256,834 A | 3/1981 | Zuk et al. | | 435/7 |
| 4,258,001 A | 3/1981 | Pierce et al. | | 422/56 |
| 4,313,734 A | 2/1982 | Leuvering | | 23/230 B |
| 4,348,207 A | 9/1982 | Cappel | | 23/230 B |
| 4,366,241 A | 12/1982 | Tom et al. | | 435/7 |
| 4,373,932 A | 2/1983 | Gribnau et al. | | 436/501 |
| 4,411,518 A | 10/1983 | Meserol et al. | | 356/39 |
| 4,419,453 A | 12/1983 | Dorman et al. | | 436/534 |
| 4,420,353 A | 12/1983 | Levine | | 156/227 |
| 4,435,504 A | 3/1984 | Zuk et al. | | 435/7 |
| 4,446,232 A | 5/1984 | Liotta | | 435/7 |
| 4,459,358 A | 7/1984 | Berke | | 436/170 |
| 4,477,575 A | 10/1984 | Vogel et al. | | 436/170 |
| 4,486,530 A | 12/1984 | David et al. | | 435/7 |
| 4,487,839 A | 12/1984 | Kamentsky | | 436/518 |
| 4,496,654 A | 1/1985 | Katz et al. | | 435/7 |
| 4,503,143 A | 3/1985 | Gerber et al. | | 435/7 |
| 4,508,829 A | 4/1985 | Sulitzeanu | | 436/510 |
| 4,515,889 A | 5/1985 | Klose et al. | | 435/4 |
| 4,537,861 A | 8/1985 | Elings et al. | | 436/518 |
| 4,545,843 A | 10/1985 | Bray | | 156/322 |
| 4,552,839 A | 11/1985 | Gould et al. | | 435/7 |
| 4,590,169 A | 5/1986 | Cragle et al. | | 436/523 |
| 4,594,327 A | 6/1986 | Zuk | | 436/514 |
| 4,623,461 A | 11/1986 | Hossom et al. | | 210/445 |
| 4,624,929 A | 11/1986 | Ullman | | 436/179 |
| 4,632,901 A | 12/1986 | Valkirs et al. | | 435/5 |
| 4,639,419 A | 1/1987 | Olson et al. | | 435/5 |
| 4,654,309 A | 3/1987 | Milnar et al. | | 922/56 |
| 4,690,907 A | 9/1987 | Hibino et al. | | 436/514 |
| 4,703,017 A | 10/1987 | Campbell et al. | | 436/501 |
| 4,756,828 A | 7/1988 | Litman et al. | | 435/7.9 |
| 4,757,004 A | 7/1988 | Houts et al. | | 435/7.9 |
| 4,761,381 A | 8/1988 | Blatt et al. | | 436/165 |
| 4,770,853 A | 9/1988 | Bernstein | | 422/58 |
| 4,772,550 A | 9/1988 | Greenquist | | 435/7 |
| 4,778,751 A | 10/1988 | El Shami et al. | | 435/7 |
| 4,803,170 A | 2/1989 | Stanton et al. | | 436/518 |
| 4,806,311 A | 2/1989 | Greenquist | | 422/56 |
| 4,806,312 A | 2/1989 | Greenquist | | 422/56 |
| 4,853,335 A | 8/1989 | Olsen et al. | | 436/527 |
| 4,857,453 A | 8/1989 | Ullman et al. | | 435/7 |
| 4,859,612 A | 8/1989 | Cole et al. | | 436/523 |
| 4,861,711 A | 8/1989 | Friesen et al. | | 436/7 |
| 4,868,108 A | 9/1989 | Bahar et al. | | 435/7 |
| 4,891,313 A | 1/1990 | Berger et al. | | 436/7 |
| 4,916,056 A | 4/1990 | Brown, III et al. | | 435/7 |
| 4,920,046 A | 4/1990 | McFarland et al. | | 435/7 |
| 4,954,319 A | 9/1990 | Koizumi et al. | | 422/67 |
| 4,956,302 A | 9/1990 | Gordon et al. | | 436/161 |
| 4,960,691 A | 10/1990 | Gordon et al. | | 435/6 |
| 4,962,023 A | 10/1990 | Todd et al. | | 435/7 |
| 4,963,468 A | 10/1990 | Olson | | 435/7 |
| 4,981,785 A | 1/1991 | Nayak | | 435/7 |
| 4,981,786 A | 1/1991 | Dafforn et al. | | 435/7 |
| 4,999,285 A | 3/1991 | Stiso | | 435/7.9 |
| 5,006,474 A | 4/1991 | Horstman et al. | | 422/56 |
| 5,030,558 A | 7/1991 | Litman et al. | | 435/7.91 |
| 5,039,607 A | 8/1991 | Skold et al. | | 435/7.5 |
| 5,075,078 A | 12/1991 | Osikowicz et al. | | 422/56 |
| 5,096,836 A | 3/1992 | Macho et al. | | 436/169 |
| 5,120,504 A | 6/1992 | Petro-Roy et al. | | 422/58 |
| 5,120,643 A | 6/1992 | Ching et al. | | 435/7.92 |
| 5,141,850 A | 8/1992 | Cole et al. | | 436/525 |
| 5,149,622 A | 9/1992 | Brown et al. | | 425/5 |
| 5,160,486 A | 11/1992 | Schlipfenbacher et al. | | 422/56 |
| 5,164,294 A | 11/1992 | Skold et al. | | 435/7.5 |
| 5,238,847 A | 8/1993 | Steinbiss et al. | | 436/64 |
| 5,248,619 A | 9/1993 | Skold et al. | | 436/514 |
| 5,275,785 A | 1/1994 | May et al. | | 422/56 |
| 5,354,692 A | 10/1994 | Yang et al. | | 436/514 |
| 5,356,782 A | 10/1994 | Moorman et al. | | 435/7.9 |
| 5,384,264 A | 1/1995 | Chen et al. | | 436/525 |
| 5,403,706 A | 4/1995 | Wilk et al. | | 435/4 |
| D361,842 S | 8/1995 | Nazareth et al. | | D24/225 |
| D369,868 S | 5/1996 | Nazareth et al. | | D24/225 |
| 5,591,645 A | 1/1997 | Rosenstein | | 436/514 |
| 5,602,040 A | 2/1997 | May et al. | | 436/514 |
| 5,656,503 A | 8/1997 | May et al. | | 436/514 |
| 5,686,315 A | 11/1997 | Pronovost et al. | | 436/510 |
| 5,712,170 A | 1/1998 | Kouvonen et al. | | 436/518 |
| 5,712,172 A | 1/1998 | Huang et al. | | 436/518 |
| 5,714,389 A | 2/1998 | Charlton et al. | | 436/514 |
| 5,728,587 A | 3/1998 | Kang et al. | | 436/514 |
| 5,739,041 A | 4/1998 | Nazareth et al. | | 436/518 |
| 6,046,057 A | 4/2000 | Nazareth et al. | | 436/514 |
| 6,319,676 B1 | 11/2001 | Nazareth | | 435/7.5 |

FOREIGN PATENT DOCUMENTS

| | | |
|---|---|---|
| AU | 679279 | 3/1995 |
| DE | 43 14 493 A1 | 11/1994 |
| DE | A 43 14 493 | 11/1994 |
| EP | 0 032 270 A1 | 7/1981 |
| EP | 0 063 810 A1 | 11/1982 |
| EP | 0 088 636 A2 | 9/1983 |
| EP | 0 158 746 A2 | 10/1985 |
| EP | 0 164 180 A1 | 12/1985 |
| EP | 0 191 640 A2 | 8/1986 |
| EP | 0 192 320 A1 | 8/1986 |
| EP | 0 201 079 A2 | 11/1986 |
| EP | 0 212 599 B1 | 3/1987 |
| EP | 0 217 403 A2 | 4/1987 |
| EP | 0 225 054 A1 | 6/1987 |
| EP | 0 250 137 A2 | 12/1987 |
| EP | 0 258 963 A2 | 3/1988 |
| EP | 0 271 204 A2 | 6/1988 |
| EP | 0 284 232 A1 | 9/1988 |
| EP | 0 306 336 A2 | 3/1989 |
| EP | 0 320 240 B1 | 6/1989 |
| EP | 0 337 082 A1 | 10/1989 |
| EP | 0 349 215 B1 | 1/1990 |
| EP | 0 420 021 A2 | 4/1991 |
| EP | 0 505 636 A1 | 9/1992 |
| EP | 0 560 411 A3 | 9/1993 |
| EP | 0 582 231 A1 | 2/1994 |
| EP | 0 810 436 A1 | 3/1997 |
| EP | 0 383 619 B1 | 4/1997 |
| GB | 2 016 687 A | 9/1979 |
| GB | 2 204 398 B | 11/1988 |
| WO | WO 86/03839 | 7/1986 |
| WO | WO 87/02774 | 5/1987 |
| WO | WO92/01226 | 1/1992 |
| WO | WO 94/01775 | 1/1994 |
| WO | WO 94/15215 | 7/1994 |

OTHER PUBLICATIONS

G. Frens, "Controlled Nucleation for the Regulation of the Particle Size in Monodisperse Gold Suspensions" *Nature Physical Science 241*:20-22 (1973).

T.C.J.Gribnau et al., "Particle-Labelled Immunoassays: A Review" *Journal of Chromatography 376*:175-189 (1986).

H.W. Leuvering et al., "Optimization of a Sandwich Sol Particle Immunoassay for Human Chorionic Gonadotrophin" *Journal of Immunological Methods 62*(1):175-184 (1983).

International Search Report dated Aug. 28, 1996 for application PCT/US96/06086, filed Jan. 5, 1996.

DIAGNOSTIC DETECTION DEVICE AND METHOD

This application is a continuation of U.S. application Ser. No. 09/951,007 filed Sep. 12, 2001, now U.S. Pat. No. 6,767,714, which is a divisional of U.S. application Ser. No. 08/432,894, filed May 2, 1995, now U.S. Pat. No. 6,319,676, the disclosures of each of which are incorporated by reference herein.

BACKGROUND OF THE INVENTION

The present invention relates to assays for an analyte, such as an antigen, in a liquid sample, such as body fluid. More particularly, the present invention relates to a method and device for the detection of an analyte in a body fluid using a lateral flow test cell containing a novel biphasic chromatographic substrate.

Many types of ligand-receptor assays have been used to detect the presence of various substances in body fluids such as urine or blood. These assays typically involve antigen-antibody reactions, synthetic conjugates comprising enzymatic, fluorescent, or visually observable tags, and specially designed reactor chambers. In most of these assays, there is a receptor (e.g. an antibody) which is specific for the selected antigen, and a means for detecting the presence and/or amount of the antigen-antibody reaction product. Most current tests are designed to make a quantitative determination, but in many circumstances all that is required is a positive/negative indication. Examples of such qualitative assays include blood typing, pregnancy testing and many types of urinalysis. For these tests, visually observable indicia such as the presence of agglutination or a color change are preferred.

The positive/negative assays must be very sensitive because of the often small concentration of the ligand of interest in the test fluid. False positives can be troublesome, particularly with agglutination and other rapid detection methods such as dipstick and color change tests. Because of these problems, sandwich assays and other sensitive detection methods which use metal sols or other types of colored particles have been developed. These techniques have not solved all of the problems encountered in rapid detection methods, however. It is an object of the present invention to provide an improved detection device and method having greater sensitivity and discrimination for analytes of interest. Another object of the invention is to provide an assay device which is simpler to manufacture.

SUMMARY OF THE INVENTION

The present invention provides a rapid, sensitive device and method for detecting the presence of analytes in body fluids. The method and device have high sensitivity and result in virtually no false positives. Use of the present device and method provides an assay system which involves a minimal number of procedural steps, and reproducibly yields reliable results even when used by untrained persons.

The device and method utilize a unique biphasic chromatographic medium which enhances the speed and sensitivity of the assay. According to the present invention, a biphasic substrate element is provided comprising a release medium joined to a capture medium located downstream of said release medium. The release and capture media preferably comprise two different materials or phases having different specific characteristics. The two phases are joined together to form a single liquid path such that a solvent front can travel unimpeded from the proximal (upstream) end of the release medium to the distal (downstream) end of the capture medium.

The release medium comprises a bibulous, hydrophilic material, such as absorbent paper. Preferred materials for use as a release medium include cotton linter paper, cellulosic paper, or paper made of cellulose together with a polymeric fibrous material, such as polyamide or rayon fibers, and glass fiber material. The primary function of the release medium is first to support and to subsequently release and transport various immunological components of the assay, such as a labeled binding member and a capturable component, both of which have specific affinity for the analyte of interest. This release and transport occurs during routine operation of the assay.

The capture medium comprises a hydrophilic polymeric material, preferably a nitrocellulose or nylon membrane. The preferred materials for use as a capture medium are microporous films or membranes which permit protein reagents to be immobilized directly on the membrane by passive adsorption without need for chemical or physical fixation. For this purpose, membranes of nitrocellulose, nylon 66 or similar materials are preferred most preferably having a pore size in the range of from about 5μ to about 20μ. The nitrocellulose membrane may be nitrocellulose alone or a mixed ester of nitrocellulose. The nitrocellulose membrane preferably is coated or laminated onto a translucent or transparent polymeric film to provide physical support for the membrane. In a currently preferred embodiment, a nitrocellulose polymer which has been cast onto a polyester film such as Mylar® is used. Alternatively, a nitrocellulose membrane laminated onto a polyester film also may be used. Other backing materials besides polyester may be used. The primary function of the capture medium is to immobilize an immunological or chemical affinity agent at one or more capture sites for capturing the reagents released from the release medium.

As stated above, the release and capture media are joined together to form a single liquid path. Reagents for detecting labeling and capturing the analyte of interest are disposed on the release and capture media. Located on the release medium is a binding member reactive with a first epitope of the analyte of interest. The binding member is labeled with a detectable marker. A capturable component is located on the release medium downstream of the binding member, which component comprises a binding agent reactive with a second epitope of the analyte and one member of an affinity pair. The capturable component is capable of forming a complex with the labeled binding member and the analyte. The labeled binding member and the capturable component both are releasably bound to the release medium such that when the solvent front created by the liquid sample being analyzed passes through the release medium, the labeled binding member and the capturable component both become solubilized by the liquid and flow with the solvent along the liquid path. In operation, if any analyte is present in the liquid sample, it reacts first with the labeled binding member, then with the capturable component as the front advances along the liquid path. By the time the solvent front reaches the capture medium section of the biphasic material, the capturable complex has formed.

The capture site located on the capture medium comprises the other member of the affinity pair specific for the capturable component. The affinity member is immobilized, preferably by simple adsorption, at the capture site, and does not advance with the solvent front.

In a preferred embodiment, a control site also is located on the capture medium downstream of the capture site. The control site has immobilized thereon a binding agent having an affinity for the labeled binding member. The binding agent will capture any labeled binding member which is not captured at the upstream capture site. In operation, the presence of the detectable marker at the control site indicates that sorptive transport has operated properly.

The present invention further provides a device for detecting the presence of an analyte in a liquid sample. The device comprises an elongate casing housing the biphasic medium, and defining a liquid sample inlet, a reservoir volume, a test volume interposed between the inlet and reservoir volume, and a window through the casing to observe the test result. Preferably, the sample inlet and the window are located in opposite sides of the casing. The casing is adapted to receive the assay materials, which are disposed on the biphasic medium sequentially within the casing. The assay materials comprise an optional sample absorbent, the biphasic chromatographic substrate and a reservoir absorbent. The chromatographic medium is positioned within the casing such that the capture site, and the control site if applicable, are visible through the window. The sample absorbent, biphasic chromatographic substrate and reservoir absorbent are in fluid communication and together form a liquid path.

In a currently preferred embodiment, the device comprises a casing defining a sample inlet, a test volume and reservoir volume. Disposed within the casing are a sample absorbent, the biphasic chromatographic substrate and reservoir absorbent. The sample absorbent is disposed within the casing opposite the sample inlet. Located downstream of the sample absorbent is the biphasic chromatographic substrate comprising a release medium and a capture medium joined together to form a single liquid path. The release medium preferably comprises sorbent paper, and the capture medium preferably comprises nitrocellulose membrane. The release and capture media preferably are both laminated onto a transparent plastic film or sheet. Disposed on said release medium is (i) a binding member comprising a specific binding protein, e.g., a monoclonal antibody reactive with a first epitope of said analyte, said antibody being labeled with a visually detectable marker such as colloidal gold particles; and (ii) a capturable component comprising a biotinylated binding protein, e.g., an antibody preferably disposed downstream of said labeled antibody. The biotinylated antibody is reactive with a second epitope of the analyte and is capable of forming a complex with the labeled antibody and the analyte. Disposed on the capture medium is a capture site for capturing and immobilizing the complex. The capture site has immobilized thereon a capture component which has a high affinity for the biotin portion of the complex, preferably streptavidin.

The biphasic chromatographic medium preferably further comprises a control site disposed on the capture medium downstream of said capture site. The control site has immobilized thereon an agent capable of capturing said labeled antibody. The primary function of the control site is to capture and immobilize labeled antibody which has not been captured at the capture site. In the currently preferred embodiment, the control site has immobilized thereon polyclonal antisera specific for the labeled antibody. The appearance of color from the gold particles at the control site indicates proper functioning of the test, irrespective of the presence or absence of analyte in the sample. Both the capture and control sites must be visible through the window of the casing.

In the method of the invention, the proximal end of the biphasic substrate is contacted with the liquid sample being analyzed. The liquid sample travels impelled by surface effects such as by capillary action along the liquid path formed by the substrate. If the analyte of interest is present in the sample, it sequentially reacts with the labeled binding member and the capturable component, forming the capturable complex, followed by reaction of the complex with the immobilized capture component at the capture site. This process results in the labeled complex accumulating at the capture site. The presence of the analyte is determined by observing the presence of the detectable marker at the capture site. If no analyte is present in the sample, the capturable complex does not form and no detectable marker will be present at the capture site. If a control site is present, the unbound complex or the free labeled binding member will accumulate at the control site.

The method of the invention also may be designed to exploit conventional "sandwich" or "competitive" techniques. In the case of the sandwich technique, the labeled binding member comprises an antibody which binds to an epitope on the analyte of interest to form a labeled antibody-antigen complex. This complex then migrates to the capture site to react with a capturable component which, in this embodiment, comprises a second antibody specific for a second epitope of said analyte. For example, in the case of biotin, the affinity member may be streptavidin. At the capture site, the analyte and labeled antibody reacts with the immobilized capture member to form a "sandwich" of the second antibody, analyte and labeled antibody. This sandwich complex is progressively produced at the capture site as sample continuously passes by. As more and more labeled conjugate is immobilized at the capture site, the colored particles aggregate and become visible through the window of the casing, indicating the presence of the analyte in the liquid sample. Both in the presence or absence of a detectable level of analyte, the colored particles gather at the control site which also is visible through the window.

In the case of the competitive technique, a known amount of the analyte of interest is present on the release medium disposed upstream of an antibody specific for it. The analyte present in the release medium is labeled. The labeled analyte on the release medium may comprise, for example, an authentic sample of the analyte, or a fraction thereof which has comparable affinity for the antibody. As the liquid sample is transported along the release medium, the labeled analyte present on the release medium and any unlabeled analyte present in the sample compete for sites of attachment to the antibody. If no analyte is present in the sample, labeled analyte-antibody aggregates at the capture site, and the presence of color indicates the absence of detectable levels of analyte in the sample. If analyte is present, the amount of labeled analyte which binds at the test site is reduced because of binding of analyte in the sample with the antibody, and no color, or a paler color, develops.

Alternatively, the system described for "sandwich" assay may be used. The antibody specific for the analyte is biotinylated, with steptavidin being immobilized at the capture site.

The use of the colored particle detection system in combination with the unique biphasic substrate enables construction of a family of extremely sensitive assay systems which minimize the occurrence of false positives and which can be used effectively by untrained persons.

BRIEF DESCRIPTION OF THE FIGURES

The present invention will now be more particularly described with reference to and as illustrated in, but in no manner limited to, the accompanying drawings, in which.

In the drawings, like reference characters in the respective drawn Figures indicate corresponding parts.

DETAILED DESCRIPTION OF THE INVENTION

Figure 1A:
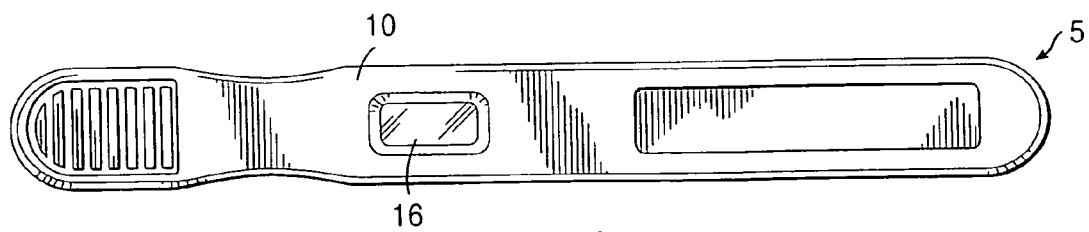
FIG. 1A is a top view of an embodiment of a test cell useful in the device and process of the present invention showing the indicator window.
Figure 1B:
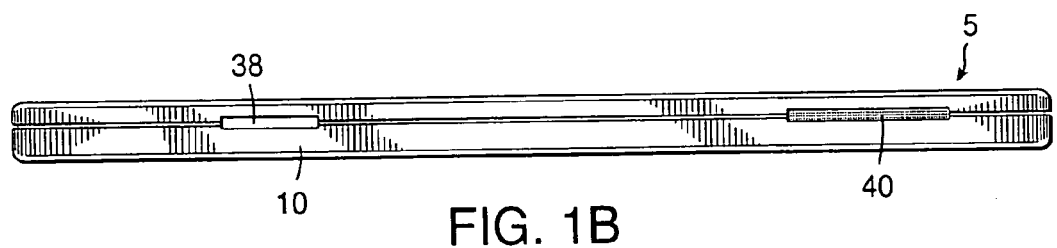
FIG. 1B is a longitudinal side view of the device of FIG. 1A.
Figure 1C:
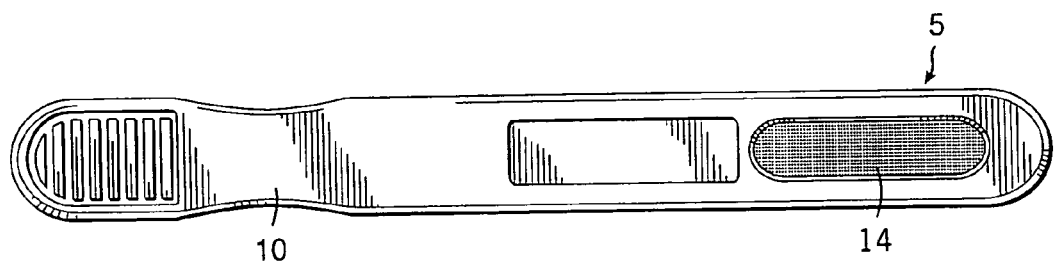
FIG. 1C is a bottom view of the device of FIG. 1A.
Figure 1D:
FIG. 1D is a tail end view of the device of FIG. 1A.
Figure 1E:
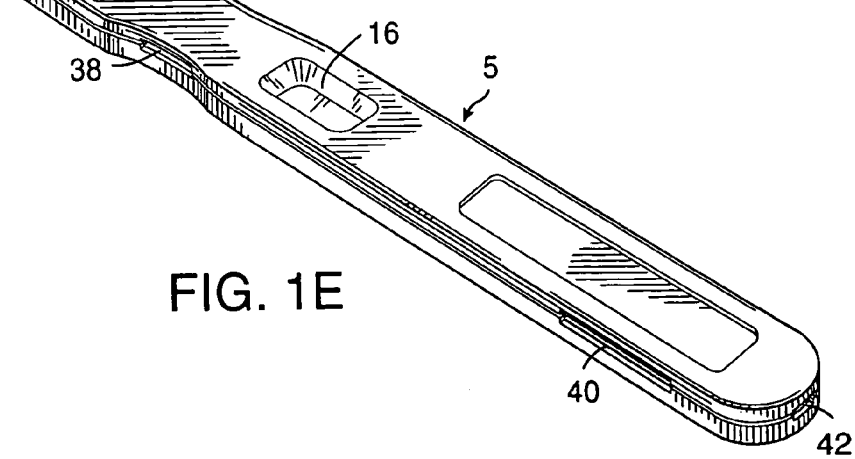
FIG. 1E is a perspective view of a currently preferred device constructed in accordance with the present invention.

The method of the invention involves the use of a novel biphasic chromatographic substrate to achieve an easily readable, sensitive, reproducible indication of the presence of an analyte, such as human chorionic gonadotropin (hCG), or luteinizing hormone (LH), in a test sample such as, for example, a human urine sample. The method and device also may be used to detect the presence of infectious agents in blood, plasma, mucus or other body fluid.

The biphasic chromatographic substrate of the present invention forms the basis for immunologically based diagnostic tests for the detection of various analytes. Use of the substrate in a diagnostic device enables the operator to determine with high accuracy and sensitivity the presence or absence of a biological marker which is indicative of a physiological condition or state.

The biphasic chromatographic substrate involves the union of two different media, each with a specific function. The release medium has disposed thereon two dry, diffusible reagents: a binding member specific to a particular site on the analyte labeled with colloidal gold or other direct label, and a capturable component comprising a binding member specific for a different site on the analyte conjugated to one member of an affinity pair. Upon reconstitution when in contact with the test solution, and in the presence of the analyte, the diffusible reagents react with the analyte to form a diffusible sandwich which is transported by capillary action to the capture medium. The capture medium contains two dry, non-diffusible reagents: a capture component comprising the other member of the affinity pair and a reagent specific for the labeled binding member. Upon diffusion into the capture medium, the diffusible sandwich becomes concentrated by the interaction of the capture affinity member with the capturable affinity moiety yielding a visual signal.

The biphasic chromatographic substrate comprises a release medium joined to a capture medium in such a way as to form a single liquid path. The release medium is formed from a substance which allows for release of indicator reagents, and the capture medium is formed from a substance which permits immobilization of reagents for detection. The release medium preferably is composed of a hydrophilic bibulous material, its primary function being to hold, release and transport various immunological parts of the test such as the labeled test component. This release and transport occurs during the routine operation of the testing procedure. Materials useful in forming the release medium include, for example, cotton linter paper such as S&S 903 and S&S GB002 (available from Schleicher and Schuell, Inc., Keene, N.H.), and BFC 180 (available from Whatman, Fairfield, N.J.), and cellulosic materials such as Grade 939 made of cellulose with polyamide and Grade 1281 made of cellulose and rayon with polyamide (available from Filtertek, Inc.) and glass fiber such as Lydall borosilicate (available from Lydall, Inc., Rochester, N.H.). The release medium preferably is coated with an aqueous solution containing bovine serum albumin (BSA) and a nonionic surfactant, such as Triton X-100 (available from Rohm & Haas Co., Philadelphia, Pa.) in order to prevent nonspecific binding and facilitate release of the diffusible reagents. A combination of about 3% BSA and about 0.1% Triton X-100 is useful for this purpose.

The capture medium preferably comprises a microporous polymeric film of nitrocellulose, nylon 66, a combination of the two, or various other materials of similar nature which are known by those skilled in the art. Pore size preferably is in the range of from about 5μ to about 20μ. The primary function of the capture medium is to immobilize the non-diffusible reagents used to detect the presence of the analyte in the test. Protein reagents can be immobilized on the capture medium by adsorption, without the need for chemical or physical modifications. The nitrocellulose may comprise nitrocellulose alone or combined with an ester of nitric acid and/or other acids. In a preferred embodiment, the nitrocellulose is directly cast onto a clear polymer film. Commercially available polyester films such as those available under the tradename Mylar® are useful for this purpose (Mylar® is a trademark of the DuPont DeNemours Company). Nitrocellulose membrane may be fabricated by art-recognized techniques, including direct casting of the nitrocellulose polymer onto a polyester sheet, or by laminating a nitrocellulose film with a polyester sheet. Prelaminated or precast sheets useful in the present invention are commercially available, for example, from Millipore Corporation, Bedford, Mass. and Corning Costar, Norristown, Pa. Both media are in the form of planar strips, which are joined together to form a single flow path. In a preferred embodiment, the release medium and capture medium are joined by overlapping the downstream edge of the release medium over the upstream edge of the capture medium, then adhering the resulting biphasic material to a clear polymer film or sheet, thereby holding the media in place.

The method for manufacturing the unique biphasic chromatographic medium used in the present invention is described in detail in U.S. Pat. No. 5,846,835, which claims priority to U.S. application Ser. No. 08/434,342, the disclosures of each of which are hereby incorporated herein by reference. Briefly, the release medium and capture medium are positioned such that they overlap slightly, and an adhesive is disposed on the back of each (the back being the side opposite that which will receive the reagents). The adhesive may be any pressure sensitive or hot melt adhesive which does not fill the pores of the release or capture medium, thereby permitting unimpeded flow of the solvent front through the media. Adhesives useful in the present invention are commercially available, for example, from Adhesives Research Corp. In a currently preferred embodiment, the adhesive is disposed on a clear polymer backing. The overlapped release and capture media then are passed through the laminating rollers of a laminating machine together with the backed adhesive, forming a laminate of the capture and release media, the adhesive and the polymer backing. The resulting laminated biphasic substrate then is ready to receive the reagents, which are deposited as continuous "stripes" onto the top of the substrate. Once the reagents have been deposited and dried, if necessary, the substrate is cut into the desired size.

The diffusible and non-diffusible reagents can be applied to the release and capture media, respectively, by any well-known technique. In a currently preferred embodiment, the diffusible antibody reagents are applied to the release medium by direct application onto the surface of the medium and dried to form a narrow band. The non-diffusible reagents are applied to the capture medium by passive adsorption.

For use, the biphasic chromatographic substrate is disposed within a test device, which device also forms a part of this invention. The device comprises, at a minimum, a housing encasing the biphasic system for conducting the assay. A preferred housing configuration is shown in design application Ser. No. 29/023,294, now U.S. Pat. No. Des. 361,842, which is incorporated herein by reference. A particularly preferred embodiment of the casing is described in U.S. application Ser. No. 08/432,890, now U.S. Pat. No. 5,739,041, which is incorporated herein by reference.

The method and device of the invention cooperate to enable untrained personnel reliably to assay a liquid sample for the presence of extremely small quantities of a particular analyte, while avoiding false positives and simplifying test procedures. The invention is ideal for use in over-the-counter assay test kits which will enable a consumer to self-diagnose, for example, pregnancy, ovulation, venereal disease and other disease, infection, or clinical abnormality, which results in the presence of an antigenic marker substance in a body fluid, including determination of the presence of metabolites of drugs or toxins. The assay process and the device are engineered specifically to detect the presence of a preselected individual analyte present in a body fluid.

In addition to the biphasic chromatographic substrate the device may comprise a sample absorbent disposed within the casing proximate the chromatographic substrate and in fluid communication therewith. The sample absorbent preferably is a bibulous hydrophilic material which facilitates absorption and transport of a fluid sample to the biphasic chromatographic medium. Such materials may include cellulose acetate, hydrophilic polyester, other materials having similar properties. A combination of absorbent materials also may be used. Preferred materials include bonded cellulose acetate, bonded polyolefin or hydrophilic polyester, such as those materials commercially available from American Filtrona Company (Richmond, Va.). Other preferred materials include absorbent papers such as Grade 939 or Grade 1281, available from Filtertek, Inc. The sample absorbent preferably is coated with a buffered solution containing BSA and a nonionic surfactant, such as Triton X-100. The presence of BSA and surfactant minimize non-specific absorption of the analyte. A concentration of about 1% BSA and about 0.2% surfactant in tris buffer is effective for this purpose.

The device further may comprise a reservoir absorbent disposed downstream of the chromatographic substrate and in fluid communication therewith. By providing a reservoir of sorbent material disposed beyond the chromatographic substrate, a relatively large volume of the test liquid and any analyte it contains can be drawn through the test area to aid sensitivity. The reservoir material preferably comprises a hydrophilic material which may be the same as the upstream sample absorbent. The purpose of the reservoir absorbent is to facilitate capillary action along the chromatographic substrate and to absorb excess liquid contained within the device. The reservoir absorbent preferably compromises absorbent paper made from cotton long linter fibers, such as S&S 300, S&S 470 and S&S 900, (available from Schleicher & Schuell, Inc.) or cellulosic materials, such as Grade 3MM (available from Whatman) and Grade 320 (available from Alhstrom).

Broadly, the device and method of the invention can be used to detect any analyte which has heretofore been assayed using known immunoassay procedures, or is detectable by such procedures, using polyclonal or monoclonal antibodies or other proteins. Various specific assay protocols, reagents, and analytes useful in the practice of the invention are known per se, see, e.g., U.S. Pat. Nos. 4,313, 734, and 4,366,241.

The combination of features believed to be responsible for the excellent sensitivity and reproducibility of assays constructed in accordance with the invention is the use of the novel biphasic chromatographic substrate and the use of a metal sol or other colored particle as a marker system which permits direct visual observation of color development. A filtration means which limits the introduction to the test site of contaminants from the sample also may be included.

The assay is conducted by simply placing the inlet of the device in contact with a liquid test sample. The casing of the device may be configured to permit direct contact with a body fluid, or as a dipstick for dipping in a container of body fluid or other test solution. After contact with the test fluid, one then merely waits for the test sample to pass through the biphasic chromatographic substrate and into reactive contact with the test site (and optionally one or more control sites) visible through a window or windows in the device's exterior casing. In a preferred embodiment, the labeled binding member specific for the analyte is disposed in preserved form on the release medium in the flow path within the device. If analyte is present in the sample, it passes through the inlet and the interior of the device along the chromatographic substrate where, in the sandwich embodiment, it reacts with labeled binding protein, and a capturable component conjugated with an affinity agent. The complex formed by the analyte, labeled binding member and the affinity conjugate then reacts with a capture affinity agent immobilized at the capture site which is specific for the affinity agent on the conjugate. A complex forms at the capture site comprising immobilized capture agent-capturable conjugate-analyte-labeled binding member. The presence of the complex, and thus the analyte, is indicated by the development of color caused by aggregation of the metal sol particles at the capture site.

From the foregoing, it will be apparent that the success of the test procedure is dependent on analyte present in the sample reacting with the labeled binding member, or on reproducible competition between the analyte and the binding member for sites of attachment at the capture site. In accordance with the invention, as noted above, the labeled binding member and capturable conjugate preferably are disposed in preserved form, e.g., air dried or freeze-dried, on the release medium within the device upstream of the capture and control sites. Analyte, if any, passing up through the device and entrained within the liquid moves into contact with the labeled binding member and capturable component forming an immune complex or initiating competition in situ as flow continues, which complex ultimately is captured by reagents immobilized on the capture medium.

Referring now to the drawings, FIGS. 1A–E illustrate schematically an embodiment of a test device 5 constructed in accordance with the invention useful in explaining its principles of construction. It comprises an outer, molded casing 10 which defines a hollow, elongate enclosure. Casing 10 defines a test liquid inlet 14 and an opening 16 comprising a window through which the capture and control sites are visible. As illustrated in FIGS. 1A–E window 16 is disposed on a side of the casing 10 opposite sample inlet 14. This configuration reduces the incidence of contamination of the test site which is disposed in the interior of casing 10 and is exposed through window 16. Casing 10 further defines vent openings 38, 40 and 42 located along the sides and at the distal end of casing 10. Vent opening 38 reduces the incidence of "vapor lock" within the device during use. The presence of openings 40 and 42 help to reduce "flooding" of the chromatographic substrate, which may occur when the user applies too much sample to the device.

Figure 2:
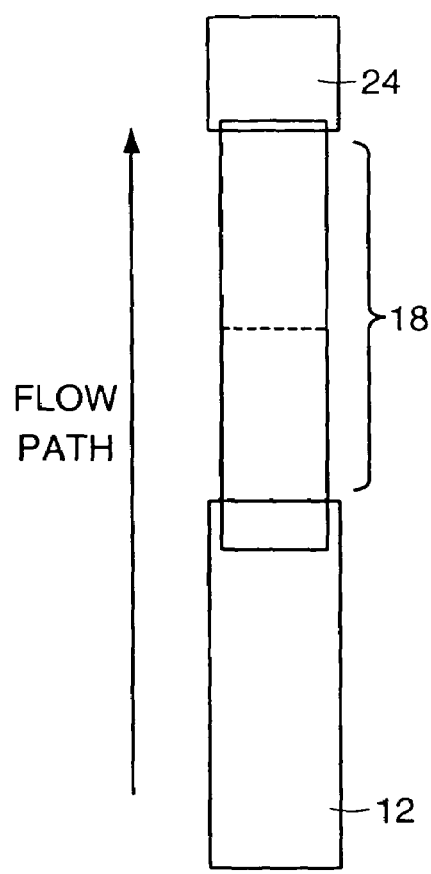
FIG. 2 is a schematic top view of the test device formed by the sample absorbent, biphasic substrate and reservoir material.

FIG. 2 illustrates schematically a preferred embodiment of the assay materials, which when the device is fully assembled, are disposed inside casing 10. The assay materials comprise absorbent material 12, biphasic chromatographic substrate 18 and reservoir material 24. The assay materials and the interior of casing 10 together define a flow path passing generally from right to left in FIGS. 1A, B and C. When the test device is placed with inlet 14 disposed within or otherwise in contact with a liquid sample, the liquid is transported by capillary action, wicking, or simple wetting along the flow path downstream through absorbent 12, along chromatographic substrate 18, and into reservoir 24, generally as depicted by the arrow. Absorbent material 12 disposed inwardly of the inlet 14 also serves as a filter which can remove from impure test samples particulate matter and interfering factors.

Figure 3:
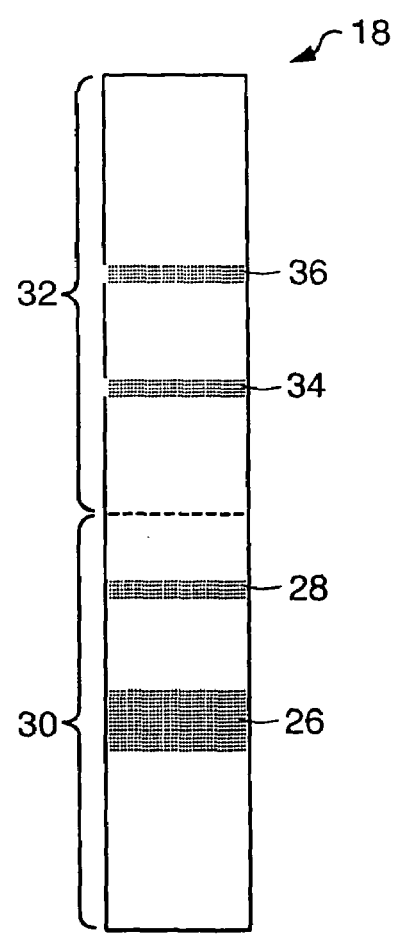
FIG. 3 is a schematic top view of a biphasic substrate of the present invention.

FIG. 3 illustrates schematically the biphasic chromatographic substrate 18, comprising a release medium 30 and a capture medium 32. Releasably disposed on release medium 30 is a band 26 of dehydrated labeled binding member, e.g., antibody-metal sol. As the liquid sample moves past band 26, the labeled binding member becomes entrained in the liquid, reconstituted, and reacts or competes with any analyte present in the liquid sample. Disposed downstream of the labeled binding member is a band 28 of dehydrated capturable complex. The capturable complex comprises a binding member which binds to a second epitope of the analyte, e.g. an antibody, and a capturable affinity component, e.g., biotin. The capturable complex also becomes entrained in the liquid sample as it advances along substrate 18.

Immobilized on capture medium 32 are, respectively, capture site 34 and control site 36. In FIG. 3, the control and capture sites are illustrated as being disposed serially along the flow path. Alternatively, the control and capture site or sites may be disposed side by side or in other spacial relationships. Capture site 34 comprises a preselected quantity of a capture affinity member specific for the capturable affinity component disposed on the release medium. The capturable component is immobilized in place within the flow path. For example, when the capturable affinity member is biotin, the capture component may be streptavidin. Control site 36 comprises immobilized antisera or antibody specific for the labeled binding member.

Figure 4:
FIG. 4 is a schematic side view of the test device of FIG. 2.

FIG. 4 illustrates schematically a side view of the operative portion of the assay materials. As shown, absorbent material 12 is disposed proximate release medium 30, and overlaps release medium 30 at one end. Release medium 30 in turn overlaps capture medium 32, which is disposed distal to release medium 30. Reservoir 24 overlaps the distal end of capture medium 32. These four components together form a single fluid path, and cooperate to cause sample liquid to flow from absorbent 12 along release medium 30 and capture medium 32 into reservoir 24.

Figure 5:
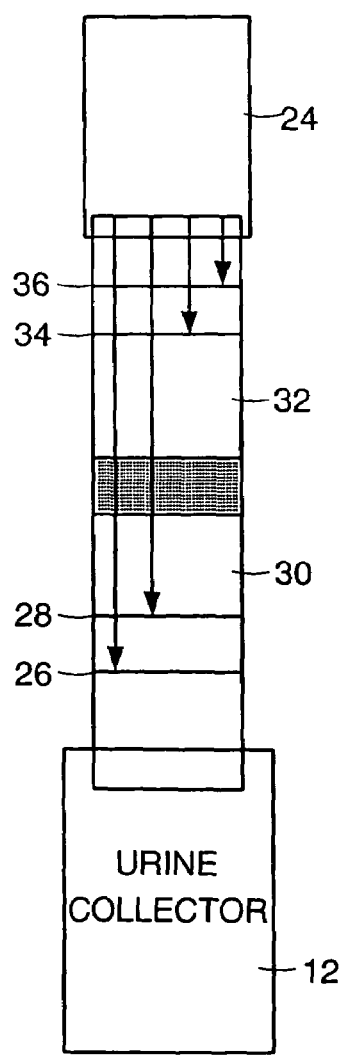
FIG. 5 is a schematic top view of the test device constructed in accordance with the invention.

FIG. 5 illustrates schematically a currently preferred embodiment of the operative portion of the assay device. As shown, release medium 30 has releasably disposed thereon a band of labeled binding member 26, which in the preferred embodiment is a monoclonal antibody conjugated to gold sol particles. Disposed downstream from band 26 is band 28 comprising the capturable component, which in the preferred embodiment is a second monoclonal antibody specific for the same analyte conjugated to biotin. Band 28 also is releasably disposed on release medium 30. Located downstream of release medium 30 is capture medium 32 having immobilized thereon capture site 34, which in the preferred embodiment is streptavidin. Located on capture medium 32 downstream of capture site 34 is control site 36, which in the preferred embodiment is polyclonal antisera specific for the labeled antibody of band 26.

The invention is not limited by the precise nature of the capture site 34 and corresponding control site 36, and in fact, control site 36 may be entirely eliminated if desired. Generally, antibody or other affinity agent can be immobilized at capture site 34 and control site 36 using absorption, adsorption, or ionic or covalent coupling, in accordance with methods known per se. Capture medium 32 preferably is selected to bind the capture reagents without the need for chemical coupling. Nitrocellulose and nylon both permit non-chemical binding of the capture component and control reagent.

As shown in FIG. 5, disposed downstream of capture medium 32 is reservoir 24 comprising a relatively large mass of absorbent or superabsorbent material. The purpose of reservoir 24 is to ensure that a reasonably large amount of test liquid is drawn across the chromatographic medium.

Figure 6:
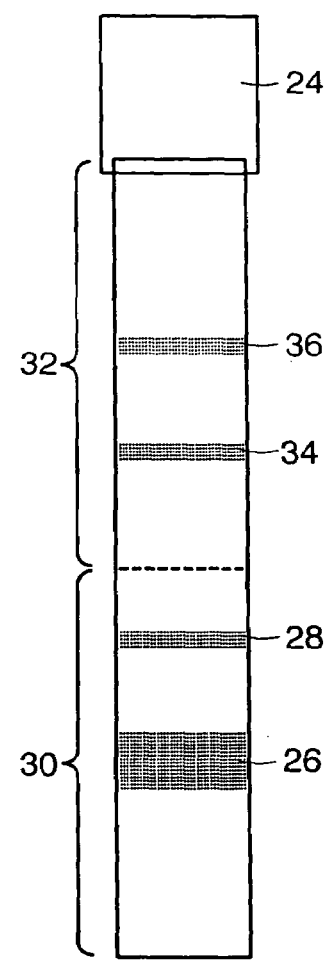
FIG. 6 is a schematic top view of a test substrate for use in a dipstick embodiment of the present invention.

FIG. 6 is a schematic illustration of an embodiment of the assay materials useful in performing dipstick assays. In the embodiment shown, sample absorbent 12 is omitted, and release medium 30 acts as the sample absorbent.

Polyclonal antisera and monoclonal antibodies or fractions thereof having specific binding properties and high affinity for virtually any antigenic substance which are useful in the present invention as binding members and capture materials are known and commercially available, or can be produced from stable cell lines using well known cell fusion and screening techniques. The literature is replete with protocols for producing and immobilizing proteins. See, for example, *Laboratory Techniques in Biochemistry and Molecular Biology*, Tijssen, Vol. 15, Practice and Theory of Enzyme immunoassays, chapter 13, The Immobilization of Immunoreactants on Solid Phases, pp. 297–328, and the references cited therein.

Metal sols and other types of colored particles useful as marker substances in immunoassay procedures are also known per se. See, for example, U.S. Pat. No. 4,313,734. For details and engineering principles involved in the synthesis of colored particle conjugates see Horisberger, Evaluation of Colloidal Gold as a Cytochromic Marker for Transmission and Scanning Electron Microscopy, Biol. Cellulaire, 36, 253–258 (1979); Leuvering et al., "Sol Particle Immunoassay", *J. Immunoassay*, 1 (1): 77–91 (1980), and Frens, "Controlled Nucleation for the Regulation of the Particle Size in Monodisperse Gold Suspensions", *Nature, Physical Science*, 241: 20–22 (1973).

In one currently preferred embodiment, the immunoassay device of the present invention is designed to detect human pregnancy. In this embodiment, the labeled binding member is a monoclonal antibody (MAb) against human chorionic gonadotropin (hCG) labeled with colloidal gold. For this purpose, MAb designated 2G9 (available from Carter-Wallace, Inc.) is preferred. Anti-hCG antibodies labeled with biotin are used for the capturable complex. Monoclonal antibodies which can be used for this purpose include the hCG specific monoclonal antibodies designated 2B2 and B109 (available from Carter-Wallace, Inc.) and CCF01 (available from Scripps Laboratory). Methods for conjugating biotin to antibodies are well-known and do not form a part of the present invention. In the present preferred embodiment, the capture site comprises streptavidin, which has a high affinity for biotin. A control site preferably is located downstream of the capture site. The control site has immobilized thereon goat anti-mouse IgG specific for the labeled anti-hCG (available from Scantibodies Laboratory).

In another preferred embodiment the present immunoassay device is designed to detect human ovulation. In this embodiment, the labeled binding member comprises MAb 2G9, which is specific for luteinizing hormone (LH) and hCG, labeled with colloidal gold. The capturable complex comprises biotinylated LH-specific MAb LH26 (available from Carter-Wallace, Inc.). The capture site preferably comprises streptavidin and the control site comprises goat anti-mouse IgG specific for the labeled MAb.

In another embodiment, the device may be adapted to detect infectious agents, such as streptococcus. In this embodiment, the labeled binding member is a rabbit polyclonal antibody specific for streptococcus labeled with colloidal gold or other direct marker. The capturable complex is the same polyclonal antibody conjugated to biotin, and the capture and control components comprise streptavidin and goat anti-rabbit IgG.

The casing 10, can take various forms. It will typically comprise an elongate casing comprising interfitting parts made of a plastic material such as polyvinyl chloride, polypropylene, polystyrene or polyethylene. Its interior flow path will contain a relatively inert material or a combination of materials suitable for facilitating transport of the liquid. Casing 10 may be adapted for direct contact with a sample liquid, as shown in the embodiment illustrated in FIGS. 1A–E, or may be adapted to dipstick form, which is not shown herein, but is well known in the art. A currently preferred design for casing 10 is described in U.S. Pat. No. Des. 361,842 and in U.S. Pat. No. 5,739,041.

From the foregoing it should be apparent that the advantages in reproducibility, sensitivity, and avoidance of false positives of assay systems constructed in accordance with the invention are traceable to a combination of features of the invention. In use, the biphasic chromatographic substrate results in efficient transport of the reagents which allows more sensitive detection of analyte.

The present invention will now be further particularly described with reference to the following Exemplification. In the Exemplification, the test devices are described with reference to FIGS. 1–6 of the accompanying drawings which have been briefly described hereinabove.

EXEMPLIFICATION

Pregnancy Test

The currently preferred configuration for the casing for the test device embodying the invention is shown in FIGS. 1A–E. The currently preferred configuration of the test materials including sample absorbent, biphasic chromatographic substrate and reservoir is shown in FIGS. 2–5. A modification of the test materials depicted in FIGS. 2–5 is shown in FIG. 6.

Figure 7:
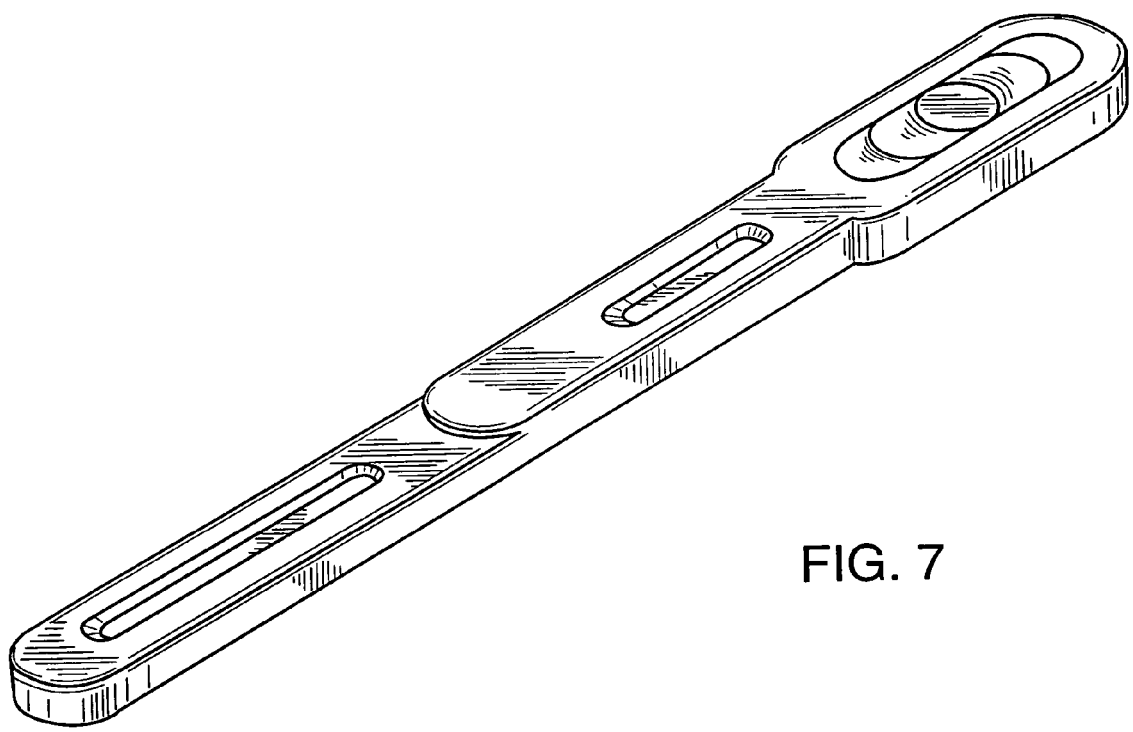
FIG. 7 is a perspective view of a dipstick embodiment of a test cell useful in the device and process of the present invention.

As shown in FIGS. 1A–E, the preferred test cell of the invention comprises a pair of interfitting polymeric parts which, when the device is assembled, define an enclosure. Casing 10 is designed to receive the biphasic chromatographic substrate and related absorbents shown in FIGS. 2–5. The assay materials are disposed within casing 10 such that the clear polymer backing 46 is disposed opposite window 16 (FIG. 1A). The results of the assay can be read through the clear polymer layer 46, and the presence of layer 46 prevents contamination of the test site during use. In operation, test liquid applied through inlet 14 is absorbed by sample absorbent 12, and soaks along chromatographic substrate 18 which defines the flow path, into reservoir volume 24. In the dipstick embodiment, the chromatographic substrate shown in FIG. 6, which lacks absorbent material 12, is disposed in a casing adapted to receive it, which is shown in FIG. 7.

In the currently most preferred embodiment, the absorbent 12 is bonded hydrophilic polyester (American Filtrona); the release medium is either S&S 903 paper or S&S GB002 paper (both from Schleicher & Schuell); the capture medium is nitrocellulose membrane cast (or laminated) onto clear polyethylene terephthalate (PET) (available from Millipore Corp.); the reservoir 24 is S&S 300 paper (Schleicher & Schuell). The release and capture media were laminated onto 5 mil clear PET precoated with an adhesive (available from Adhesives Research). The dimensions of absorbent material 12 are approximately 5.0×1.27×0.25 cm (2.0×0.5×0.1 inches) on each side. The dimensions of release medium 32 of the biphasic chromatographic substrate 18 are approximately 2.8×0.8×0.06 cm (1.1×0.32×0.025 inches), and for the capture medium, approximately 2.5×0.8×0.018 cm (1×0.32×0.007 inches). The dimensions of the reservoir absorbent pad are approximately 2.0×0.26×1.06 cm (0.8×0.1×0.4 inches). A number of these substrates were produced and further treated to adapt them to detect pregnancy by assay of urine for the presence of human chorionic gonadotropin (hCG). The test reagents were hCG monoclonal antibody 2G9 (obtained from Carter-Wallace, Inc.) labeled with colloidal gold 15–30 nm in size; biotinylated hCG specific monoclonal antibody CCF01 (obtained from Scripps Laboratory); streptavidin, lyophilized material reconstituted in phosphate buffer to a concentration of 2 mg/ml; and goat anti-mouse IgG, solution adjusted to a concentration of 1 mg/ml in phosphate buffer. The test reagents were positioned on the media as shown in FIGS. 3 and 5.

Test Protocol

Two samples of the pregnancy assay were prepared using biphasic chromatographic media as described above. One sample designated "Test 1" was prepared using as the capture medium a nitrocellulose membrane which had been laminated onto a polyester film. The other sample, designated "Test 2" was prepared using as the capture medium a nitrocellular membrane which had been cast onto a polyester backing. All other aspects of the biphasic chromatographic media were identical.

The test was carried out by applying solutions containing known quantities of commercially available hCG to the proximal end of the chromatographic media, and permitting the test solutions to proceed through capillary action through the biphasic medium.

For comparison, a commercially available pregnancy test kit (First Response™, Carter-Wallace, Inc., New York, N.Y.) was subjected to the same procedure. The commercial test kit uses a single phase chromatographic medium consisting of a hydrophilic cellulosic material. The differences between the test samples and the commercial test are shown in Table 1.

The pink color was clearly visible at 50 mIU of human chorionic gonadotropin for both test samples, but not for the commercial product. The results indicate that the test of the present invention can detect pregnancy in a human as early as the day of a missed menstrual period. In initial stages of testing, approximately 50 negative samples from various sources had been run with no false positives or even borderline cases. In contrast, at 50 mIU of hCG, the commercial pregnancy test showed a negative result.

Table 3 illustrates the amounts of reagents needed for the pregnancy test (Test 2) made using the biphasic substrate of the present invention compared to the commercial test. As shown in Table 3, tests of the present invention require significantly less reagent and (as shown in Table 2) are both more sensitive and more accurate.

TABLE 1

|  | Commercial Product | Test Samples |
| --- | --- | --- |
| Chromatographic Medium | Monophasic-consisting of hydrophilic cellulosic material | Bi-phasic-comprising a capture medium (nitrocellulose membrane) and a release medium (hydrophilic cellulosic material) |
| Reagents (Bottom to top) | Mobile reagents-<br>1. Labeled anti-hCG antibody<br>2. Biotinylated antibody<br>Capture reagents-<br>3. Streptavidin coupled to latex<br>4. Goat anti-mouse IgG coupled to latex | Mobile Reagents-<br>1. Labeled antibody<br>2. Biotinylated antibody<br>Capture reagents-<br>3. Streptavidin<br>4. Goat anti-mouse IgG |
| Mode of Immobilization of Capture Reagents | Via latex beads onto hydrophilic cellulosic material | Passive adsorption onto nitrocellulose membrane |
| Mobile Reagents | Direct application onto the hydrophilic cellulosic material | Direct application onto the hydrophilic cellulosic material |
| Upstream Reservoir | Blotting paper made of a blend of cotton linter fibers | Same |
| Chromatographic Component | Mono-phasic | Bi-phasic |
| Sample Absorbent | Two 50 mm × 12.5 mm × 5 mm cellulose acetate pads | One 50 mm × 11.4 mm × 2.5 mm hydrophilic polyester material |

The results of the test procedure are shown in Table 2:

TABLE 2

Comparison of Reaction Times for Commercial and Improved Pregnancy Tests

| hCG Level (mIU) | Commercial Rxn/time | Test 1 Using Laminated Membrane Rxn/time | Test 2 Using Mylar Cast Membrane Rxn/time |
| --- | --- | --- | --- |
| 0 | neg/1:45 | neg/1:35 | neg/1:30 |
| 25 | neg/2:06 | pos/1:15 | neg/1:45 |
| 50 | neg/1:45 | pos/0:50 | pos/0:50 |
| 100 | pos/2:00 | pos/0:40 | pos/0:30 |
| 300 | pos/2:00 | pos/0:40 | pos/0:35 |

TABLE 3

Comparison of Reagent Usage

| REAGENT | COMMERCIAL | TEST 2: IMPROVED | PERCENT DECREASE |
| --- | --- | --- | --- |
| Gold labeled antibody | 0.45 $OD_{533}$ | 0.048 $OD_{533}$ | 89 |
| Biotinylated antibody | 1 ug | 0.1 ug | 90 |
| Streptavidin | 7.8 ug | 0.8 ug | 90 |
| Goat anti-mouse IgG | 7.5 ug | 0.8 ug | 89 |

Table 4 shows the results of actual tests carried out using the present pregancy test device. All versions listed in Table 4 contain the biphasic medium and reagents described above, but differ in the configuration of casing 10. It was found, surprisingly, that certain physical modifications to casing 10, particularly the introduction of vents 38, 40 and 42 (FIGS. 1B, 1E), resulted in significant higher accuracy and fewer invalid results. The differences between the different versions shown in Table 4 is as follows:

Version 1

This version had long posts that were easily broken when the components were stored in plastic bags. The devices easily came part when dropped from a desk top.

Version 2

In this version the posts were shortened to eliminate breakage. A urine stop was added to prevent urine from bypassing the release medium and wetting the membrane.

Version 3

This version added posts to prevent the device from coming apart when dropped. Additional urine stops were included to further prevent flooding of the membrane. A crossbar was added to the top housing the push the upstream absorbent against the membrane to assist in sample flow and gold clearance.

Version 4

Version 3 devices were modified by manually cutting vents in the device. Two long side vents and one short base vent were cut in the top housing to prevent membrane flooding.

Modified Version 4

Version 4 devices were modified by cutting a window in the top housing similar to the urine collection area on the bottom housing. This device was called "two-sided"—sample could be applied to either the front or back of the device.

Version 5 represents the currently preferred embodiment of the pregnancy test device. As shown in Table 4, the tests were all completed in less than five minutes, with no invalid results.

EQUIVALENTS

From the foregoing description, one skilled in the art can easily ascertain the essential characteristics of this invention, and without departing from the spirit and scope thereof, can make various changes and modifications to adapt it to various usages and conditions. Such embodiments are intended to be included within the scope of the following claims.

The invention claimed is:

1. A device for determining the presence in a liquid sample of an analyte wherein liquid sample deposited on a proximal end of the device travels downstream along a liquid path to a distal end of the device, the device comprising:
    a biphasic substrate comprising (1) a release medium of a first material and, in fluid communication and downstream thereof, (2) a capture medium of a microporous, second, different material,
    wherein located at the release medium of the biphasic substrate for release therefrom is
    (i) a labeled conjugate comprising a binding member reactive with a first epitope of the analyte labeled with a detectable marker, and
    (ii) a capturable component reactive with a second epitope of the analyte, such that if the analyte is present in the sample, the analyte produces a complex comprising the labeled conjugate, the analyte and the capturable component, and
    located at the capture medium of the biphasic substrate is
        a capture site for capturing the complex, the capture site having immobilized thereon a capture component having a binding affinity for the capturable component.

2. The device of claim 1 further comprising a control site located downstream of the capture site, the control site having immobilized thereon an agent having a binding affinity for the labeled conjugate.

3. The device of claim 1 wherein the capture medium is laminated to or cast on a transparent polymeric material.

4. The device of claim 1 comprising a sample absorbent located upstream of the biphasic substrate at the proximal end of the device.

5. The device of claim 1 further comprising a residual absorbent located downstream of the biphasic substrate at the distal end of the device.

6. The device of claim 1 wherein the binding member of the labeled conjugate is an antibody.

7. The device of claim 1 wherein the capturable component is a biotinylated antibody.

8. The device of claim 7 wherein the immobilized capture component comprises avidin, streptavidin or an antibiotin antibody.

9. The device of claim 1 wherein the immobilized capture component comprises avidin, streptavidin, or an antibiotin antibody.

10. The device of claim 1 wherein the second material of the biphasic substrate is nitrocellulose or nylon.

11. The device of claim 1 wherein the first material of the biphasic substrate is absorbent paper.

12. The device of claim 1 wherein the release medium and the capture medium of the biphasic substrate are both immobilized on a single backing support.

13. A device for determining the presence in a liquid sample of an analyte wherein liquid sample deposited on a proximal end of the device travels downstream along a liquid path to a distal end of the device, the device comprising:
    a biphasic substrate comprising (1) a release medium of a first material and in fluid communication and downstream thereof, (2) a capture medium of a second, different material of nylon or nitrocellulose, wherein the release medium and the capture medium are both immobilized on a single backing support,
    wherein located at the release medium of the biphasic substrate for release therefrom is
    (i) a labeled conjugate comprising a first antibody that binds a first epitope of the analyte labeled with a detectable marker, and
    (ii) a capturable component comprising a biotinylated second antibody that binds a second, different epitope of the analyte, such that if the analyte is present in the sample, the analyte produces a complex comprising the labeled conjugate, the analyte and the capturable component, and
    located at the capture medium of the biphasic substrate is
        a capture site for capturing the complex, the capture site having a capture component immobilized thereon for biding the capturable component.

14. The device of claim 13 further comprising a control site located downstream of the capture site, the control site having immobilized thereon an agent having binding affinity for the labeled conjugate.

15. The device of claim 13, wherein the capture medium is laminated to or cast on a transparent polymeric material.

16. The device of claim 13 further comprising a sample absorbent located upstream of the biphasic substrate at the proximal end of the device.

17. The device of claim 13 further comprising a residual absorbent located downstream of the biphasic substrate at the distal end of the device.

18. The device of claim 13, wherein the first material of the biphasic substrate is absorbent paper.

19. The device of claim 13, wherein the capture component is avidin or streptavidin.

* * * * *